United States Patent
Springer et al.

(10) Patent No.: US 7,138,544 B2
(45) Date of Patent: Nov. 21, 2006

(54) PROCESS FOR PREPARING ALIPHATIC STRAIGHT-CHAIN AND BETA-ALKYL-BRANCHED CARBOXYLIC ACIDS

(75) Inventors: Helmut Springer, Dinslaken (DE); Frank Winsberg, Duisburg (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 11/237,294

(22) Filed: Sep. 28, 2005

(65) Prior Publication Data

US 2006/0106249 A1 May 18, 2006

(30) Foreign Application Priority Data

Nov. 16, 2004 (DE) ............... 10 2004 055 252

(51) Int. Cl.
*C07C 51/235* (2006.01)
(52) U.S. Cl. ............................................. 562/531
(58) Field of Classification Search ............... None
See application file for complete search history.

(56) References Cited

U.S. PATENT DOCUMENTS 6,800,783 B1 * 10/2004 Springer et al. ............ 562/531

FOREIGN PATENT DOCUMENTS

| DE | 732 720 | 2/1943 |
|----|---------|--------|
| DE | 16 18 589 | 2/1971 |
| DE | 43 33 323 | 4/1995 |
| DE | 10010771 | 5/2001 |
| DE | WO 01/66504 A2 * | 9/2001 |
| GB | 856962 * | 12/1960 |

* cited by examiner

*Primary Examiner*—Paul A. Zucker
(74) *Attorney, Agent, or Firm*—Charles A. Muserlian

(57) ABSTRACT

The present invention relates to a process for preparing aliphatic straight-chain and β-alkyl-branched carboxylic acids by catalytic oxidation of aldehydes by means of oxygen or oxygen-containing gas mixtures. Alkali metal carboxylates or alkaline earth metal carboxylates or a mixture thereof in an amount, calculated as alkali metal or alkaline earth metal, of from 1 mmol each to from 10 mmol each per mole of aldehyde used and also metals or compounds of metals of groups 5 to 11 of the Periodic Table of the Elements in amounts of not more than 5 ppm, based on aldehyde used, are present as catalyst.

17 Claims, No Drawings

PROCESS FOR PREPARING ALIPHATIC STRAIGHT-CHAIN AND BETA-ALKYL-BRANCHED CARBOXYLIC ACIDS

The present invention relates to a novel, catalytic process for preparing aliphatic straight-chain and β-alkyl-branched carboxylic acids from aldehydes by oxidation using oxygen or oxygen-containing gases.

Aldehydes are widely used as starting materials for the preparation of carboxylic acids. The predominant position occupied by aldehydes for this application is due to their good availability from a number of processes, including processes utilized in industry. In addition, the carbonyl group of aldehydes can easily be converted into the carboxyl group. In processes carried out in industry, the conversion of aldehydes into carboxylic acids is predominantly carried out in the presence of catalysts. Possible catalysts are predominantly salts of transition metals, in particular salts of cobalt and of manganese and also of chromium, iron, copper, nickel, silver and vanadium. Nevertheless, the formation of carboxylic acids from aldehydes is frequently associated with secondary and decomposition reactions, even when optimal temperature conditions are adhered to.

J. Prakt. Chem. vol. 14 (1961), 71–83 describes the oxidation of isononanal in the presence of cobalt acetate or manganese naphthenate. In the presence of the manganese-containing catalyst, the yield of isononanoic acid at a reaction temperature of 60° C. is only about 70%.

In the process described in DE-A 30 29 700, aliphatic monocarboxylic acids having from 6 to 9 carbon atoms are prepared by oxidizing the corresponding aldehydes by means of oxygen in pure form or by means of air. A combination of manganese and copper compounds which are soluble in the acid acts as catalyst. The metals are present in an amount in each case of from about 10 to about 2000 ppm, preferably from 200 to 600 ppm of manganese and copper, based on the weight of the liquid reaction mixture. The molar ratio of manganese to copper is from 5:1 to 0.5:1. The reaction of the starting materials is carried out in the liquid phase at temperatures of from about 50 to 80° C. and pressures in the range from about 1.4 to 10.3 bar. The process description indicates that the presence of copper and manganese compounds in the reaction product, i.e. in the carboxylic acid, is the main difficulty associated with this process. Removal of the metals requires complicated purification measures, for example precipitation of the metals using aqueous oxalic acid.

The process disclosed in U.S. Pat. No. 4,487,720 for preparing $C_5$- to $C_9$-monocarboxylic acids by oxidation of aldehydes having the same number of carbon atoms by means of pure oxygen or by means of air is likewise carried out using copper and manganese compounds as catalysts. The total amount of the metals extends over a range from 10 to 200 ppm, based on the total weight of the solution comprising aldehyde, acid and catalyst. Manganese and copper are used in a molar ratio of from about 3:1 to about 1:1. A disadvantage of this procedure is said to be the formation of copper films which occur in the purification of the acid by distillation and result in mechanical damage in the distillation apparatus. To avoid this problem, it is recommended that the distillation be carried out in the presence of oxygen.

The published German patent application 26 04 545 describes the preparation of alkylcarboxylic acids of the formula $C_nH_{2n+1}COOH$, where n is from 2 to 18, by hydroformylation, also known as the oxo process, of an olefin of the formula $C_nH_{2n}$ and direct oxidation of the reaction mixture obtained in the hydroformylation. In this context, "direct" means that no prior work-up of the hydroformylation mixture is carried out and the subsequent oxidation reaction is carried out in the presence of rhodium. The known oxidation process is employed, in particular, for the preparation of mixtures of isomeric $C_9$–$C_{16}$-fatty acids. Starting olefins for the oxo process are preferably the dimers and trimers of propene and of the butenes, including, in particular, dimeric isobutene (2,4,4-trimethyl-1-pentene). Both individual reactions of the two-stage process, i.e. both the hydroformylation and the oxidation, are catalyzed by rhodium in the form of its compounds. The rhodium concentration in the reaction mixture subjected to the oxidation is therefore determined by the relatively high rhodium content of the hydroformylation product. To ensure that the overall process is economical, it is necessary to recover the noble metal as completely as possible from the end product of the process, viz. the carboxylic acid, by means of suitable measures. In addition, it cannot be ruled out that rhodium in the prevailing concentration will promote undesirable secondary reactions during the oxidation step, since the carboxylic acid yield is, as the examples show, unsatisfactory for industrial utilization of the process.

In J. Org. Chem. 1990, 55, p. 1563 ff., LARKIN reports that the presence of catalysts in the commercial oxidation of aldehydes to carboxylic acids is considered necessary because traces of metal salts which can catalyze secondary reactions are present in the reaction mixture. The formation of the metal salts is due to corrosion of metallic plant components. The function of the catalysts is to overcompensate the action of the corrosion products.

In Ullmanns Encyklopädie der technischen Chemie, 4th edition 1975, vol. 9, reference is also made a number of times to the negative influence of metallic impurities in the starting aldehydes used for the oxidation. For example, in the oxidation of butyraldehyde to butyric acid, iron and cobalt salts dissolved in the butyraldehyde lead to increased formation of by-products (l.c., page 142, left-hand column), and in the oxidation of 2-ethylhexanal to 2-ethylhexanoic acid, heavy metal ions accelerate the decarbonylation of the starting aldehyde to form heptane (l.c., page 144, left-hand column).

It is indicated in the prior art that the action of catalyst additives depends on the structure of the aldehyde used for the oxidation. Thus, for example, DE 950 007 discloses that the oxidation of aldehydes which are branched in the α position requires the addition of small amounts of alkali metal salts of carboxylic acids in order to obtain the desired carboxylic acids in high yield and at the same time in high purity.

According to the teachings of the published Japanese patent application 53-105413, α-branched aliphatic aldehydes are oxidized by means of oxygen in the presence of lithium compounds or alkaline earth metal compounds which are used in amounts of from 0.01 to 10% by weight (based on the total reaction system) in order to prepare α-branched aliphatic carboxylic acids.

A key aspect of the procedure described in the French patent application 2 769 624 is adherence to relatively low reaction temperatures, namely temperatures in the range from 0 to 25° C. The process likewise requires the presence of alkali metal compounds or alkaline earth metal compounds as auxiliaries. The specific effects displayed by these compounds is not disclosed, i.e. whether they, as is known, merely improve the selectivity of the reaction or else possibly also increase the reaction rate at the low temperatures selected remains unanswered.

In the oxidation of α-branched aldehydes in which the carbon atom adjacent to the carbonyl carbon bears the branch, the prior art thus recommends the addition of small amounts of alkali metal carboxylates to improve the selectivity. However, such an addition is associated with an increase in the reaction time because of its inhibiting action. Among α-branched aldehydes, 2-ethylhexanal which is converted in large quantities into 2-ethylhexanoic acid is of particular economic importance.

The oxidation of aldehydes which bear the branch in the β position, i.e. on the carbon atom which is the next but one carbon atom from the carbonyl carbon, can likewise be effected with addition of a catalyst. An economically important aldehyde having a high proportion of β-alkyl-branched compounds is obtained by hydroformylation of industrially available diisobutene (2,4,4-trimethyl-1-pentene). Oxidation in the presence of rhodium as described in DE-A1-26 04 545 gives a mixture of isomeric $C_9$-fatty acids having a high proportion of 3,5,5-trimethylhexanoic acid, frequently also referred to as isononanoic acid. The oxidation of β-alkyl-branched aldehydes, for example of isovaleraldehyde, in the presence of alkali metal carboxylates or alkaline earth metal carboxylates is known from DE-A1-732 720.

According to the teachings of DE-C1-100 10 771, linear aldehydes can be converted into the corresponding carboxylic acids in the presence of transition metals or compounds thereof.

The patent DE-C1-100 10 771 likewise discloses the use of a mixture of alkali metal salts and transition metals in the oxidation of 2-methylbutanal as α-branched aldehyde.

The known catalytic processes for the oxidation of aliphatic straight-chain aldehydes and of β-alkyl-branched aldehydes to form the corresponding carboxylic acids do not yet fully meet the technical and economic demands made on modern, industrial processes. The use of transition metal catalysts often results in the occurrence of undesirable secondary reactions which reduce the selectivity, so that the yield of the desired carboxylic acids suffers despite a high conversion. Although the addition of alkali metal carboxylates and/or alkaline earth metal carboxylates improves the selectivity behavior, it has an adverse effect on the conversion behavior.

It is therefore an object of the invention to provide a process for the oxidation of aliphatic straight-chain aldehydes and of β-alkyl-branched aldehydes which does not have the abovementioned disadvantages and leads to the desired carboxylic acids with high selectivity at high aldehyde conversions. The result sought is the production of straight-chain carboxylic acids and of β-alkyl-branched carboxylic acids in high yield and purity from the corresponding aldehydes.

This object is achieved by a process for preparing aliphatic straight-chain and β-alkyl-branched carboxylic acids having from 5 to 13 carbon atoms by oxidation of the corresponding aldehydes by means of oxygen or oxygen-containing gas mixtures at from 20 to 100° C. In the process of the invention, the oxidation of the aldehydes is carried out in the presence of alkali metal carboxylates or alkaline earth metal carboxylates or a mixture thereof in an amount, calculated as alkali or alkaline earth metal, of from 1 mmol each to 10 mmol each per mole of aldehyde used and in the presence of from 0.1 to 5.0 ppm of a metal of Groups 5 to 11 of the Periodic Table of the Elements or the corresponding amount of a compound of such a metal or a mixture of such metals and/or metal compounds, based on the aldehyde used.

Surprisingly, aliphatic straight-chain or β-alkyl-branched aldehydes can be reacted with pure oxygen or oxygen-containing gas mixtures to form the corresponding carboxylic acids with high selectivity combined with a high conversion in the presence of small amounts of alkali metal carboxylates or alkaline earth metal carboxylates and in the presence of small amounts of selected metals or compounds of these metals.

An essential feature of the novel process is the simultaneous presence of alkali metal carboxylates or alkaline earth metal carboxylates or a mixture thereof and the catalytically active metals in the oxidation mixture. It has surprisingly been found that the simultaneous presence of alkali metal carboxylates or alkaline earth metal carboxylates and the catalytically active metals in the oxidation mixture enables the selectivity in the oxidation of straight-chain aliphatic aldehydes to be improved still further at a high conversion, so that, overall, a higher yield of straight-chain, aliphatic carboxylic acids is observed compared to a procedure in which the oxidation of straight-chain aliphatic aldehydes is carried out only with addition of metal as described in DE-C1-100 10 771. In the oxidation of β-alkyl-branched aldehydes, too, the aldehyde conversion and the selectivity to the desired carboxylic acids can be increased further compared to the teachings of DE-C1-100 10 771, so that the procedure according to the invention leads to a significant increase in yield in the oxidation of β-alkyl-branched aldehydes.

The amounts of alkali metal carboxylates or alkaline earth metal carboxylates, calculated as alkali or alkaline earth metal, used per mole of aldehyde are from 1 mmol each to 10 mmol each. Additions of smaller amounts give no advantages while additions of over 10 mmol of alkali metal carboxylates or alkaline earth metal carboxylates per mole of aldehyde, calculated as alkali or alkaline earth metal, give results corresponding to those observed in the process variant carried out without addition of alkali metal carboxylates or alkaline earth metal carboxylates.

The total amount of alkali metal carboxylates or alkaline earth metal carboxylates added, including carboxylates in the form of their mixtures, should not exceed a maximum total value of 30 mmol of alkali and/or alkaline earth metal, based on 1 mol of aldehyde.

Particularly high yields are achieved when from 1 to 8 and in particular from 1 to 5 mmol of alkali metal carboxylate or alkaline earth metal carboxylate, calculated as alkali or alkaline earth metal, is added per mole of aldehyde.

It is not necessary for the alkali metal carboxylates or alkaline earth metal carboxylates to be used as a uniform compound. It is likewise possible to use mixtures of these compounds and also mixtures of alkali metal carboxylates and alkaline earth metal carboxylates, but it is advantageous to use the carboxylates of the carboxylic acids formed in the oxidation. However, preference is given to using uniform compounds, for example lithium, potassium, sodium, magnesium, calcium or barium carboxylates, e.g. potassium isononanoate, sodium isononanoate, calcium isononanoate, barium isononanoate, potassium pentanoate, sodium pentanoate, calcium pentanoate or barium pentanoate.

In general, a solution comprising alkali metal carboxylate or alkaline earth metal carboxylate is prepared by neutralizing an aqueous solution comprising the alkali metal compound or alkaline earth metal compound with an excess of the particular desired carboxylic acid and this solution is added to the aldehyde to be oxidized. Suitable alkali metal or alkaline earth metal compounds are, in particular, the hydroxides, carbonates or hydrogencarbonates.

However, it is also possible to generate the alkali metal carboxylates or alkaline earth metal carboxylates in the reaction mixture by adding alkali metal or alkaline earth metal compounds which are converted into the carboxylates under the reaction conditions to the reaction mixture. For example, alkali metal or alkaline earth metal hydroxides, carbonates, hydrogencarbonates or oxides can be used in the process of the invention. They can be added either in solid form or as an aqueous solution.

According to the invention, at least one metal from groups 5 to 11 of the Periodic Table of the Elements (version in accordance with the IUPAC recommendation of 1985) or at least one compound of such a metal is/are added as catalyst to the oxidation mixture in addition to the alkali metal carboxylate or alkaline earth metal carboxylate. If metals in elemental form are used as catalysts, it is advisable to add them in finely divided form to the reaction mixture. Instead of metals in elemental form, it is also possible to employ compounds of the metals as catalysts. The type of compounds is not subject to any restriction. However, unless there are particular reasons, preference will be given to compounds which are soluble from the beginning in the reaction mixture so as to avoid a delay in commencement of the reaction due to prior formation of a soluble and thus particularly active metal compound.

Metals of groups 5 to 11 which are catalytically active even in a very small amount include vanadium, chromium, molybdenum, iron, cobalt, nickel, ruthenium, rhodium, palladium, copper, preferably chromium, iron, nickel, rhodium and in particular iron and rhodium. As compounds which are soluble in the reaction mixture, use is made of salts, in particular salts of organic acids, preferably carboxylates of the acids which are the result of the oxidation reaction. Other suitable compounds of the metals used according to the invention are complexes, e.g. acetylacetonates, metal carbonyls, hydridometal carbonyls, also carbonyl compounds comprising further ligands such as phosphines substituted by organic radicals, e.g. arylphosphines, alkylphosphines, arylalkylphosphines, in addition to carbon monoxide and possibly hydrogen. An example of such ligands is triphenylphosphine.

It is not necessary to use the catalytically active metals or the compounds containing catalytically active metals as pure substances. Instead, it is also possible to use mixtures of the metals mentioned or the metal compounds and likewise mixtures of metals and metal compounds as catalysts.

A maximum weight ratio of metal to aldehyde to be oxidized is to be adhered to in the process of the invention. According to the invention, the upper limit to this ratio is 5 ppm, i.e. 5 parts by weight of catalyst metal per $10^6$ parts by weight of aldehyde. It has been found to be particularly useful to employ from 0.2 to 3 parts by weight of catalyst metal, preferably from 0.5 to 2 parts by weight of catalyst metal, per $10^6$ parts by weight of aldehyde. The above-described ratios of catalyst metal to aldehyde also apply when using metal compounds, i.e. the amount of the compound to be used is calculated according to its metal content. An analogous situation applies to the use of mixtures of various catalytically active metals or metal compounds and of mixtures of metals and metal compounds.

The amounts of metal employed ensure a reaction rate sufficient for industrial requirements. However, they do not give rise to undesirable secondary reactions, so that the aldehydes are converted virtually exclusively into the corresponding carboxylic acids. In addition, the amounts of metal used are so small that they do not have to be recovered or moved from the reaction product either from the point of view of the economics of the process, e.g. when using expensive noble metals, or with a view to the purity of the carboxylic acids required for various fields of application.

The process of the invention is carried out in a temperature range from 20 to 100° C. It is preferably carried out at from 20 to 80° C., in particular from 40 to 80° C. The temperature conditions, viz. constant or variable temperature, can be matched to the individual requirements of the starting material and the circumstances of the reaction.

The reactants are preferably reacted at atmospheric pressure. However, the use of superatmospheric pressure is not ruled out. The reaction is usually carried out in a range from atmospheric pressure to 1.0 MPa, preferably from atmospheric pressure to 0.8 MPa.

The reaction time required to convert aldehydes into carboxylic acids by the process of the invention depends, inter alia, on the reaction temperature, the type of starting materials and the ratio of the reactants to one another. It is normally from 30 minutes to 20 hours, in particular from 2 to 8 hours.

The oxidation of aliphatic straight-chain or β-alkyl-branched aldehydes having from 5 to 13 carbon atoms is at the center of the novel process. For the purposes of the present invention, β-alkyl-branched aldehydes include aldehydes which bear further side groups on the carbon skeleton in addition to the β-alkyl branch. The origin of the aldehydes is not restricted to particular preparative processes. Owing to their ready availability, aldehydes obtained by means of the oxo process, i.e. by reaction of olefins having from 4 to 12 carbon atoms with carbon monoxide and hydrogen, are preferred. In this context, it is not critical which particular embodiment of the oxo process has been employed for obtaining the aldehydes, i.e. whether the reaction has been catalyzed by, for example, cobalt or rhodium, whether the metals were used alone or together with complexing agents and the catalyst was homogeneously dissolved in the reaction mixture or formed a separate, heterogeneous phase.

The process of the invention is particularly useful for preparing isononanoic acid from the reaction product of the oxo process carried out using diisobutylene. The industrially available reaction product of the hydroformylation of diisobutylene comprises 3,5,5-trimethylhexanal as main constituent together with small amounts of 3,4,4- and 3,4,5-trimethylhexanal. In addition, small amounts of aldehydes which are not branched in the β position, e.g. 2,5,5-trimethylhexanal, 4,5,5,-trimethylhexanal and 6,6-dimethylheptanal, are present. The oxidation of this industrially available mixture of isomeric nonanals by the process of the invention leads to a high conversion together with outstanding selective formation of isononanoic acid.

The process of the invention is likewise very suitable for the oxidation of n-pentanal, n-heptanal, n-nonanal and isovaleraldehyde to the corresponding carboxylic acids.

In the process of the invention, molecular oxygen or gas mixtures comprising molecular oxygen are used as oxidant. Further constituents of such gas mixtures are inert gases, e.g. nitrogen, noble gases and carbon dioxide. The proportion of inert constituents of the oxygen-containing gas mixture is up to 90% by volume, in particular from 30 to 80% by volume. Preferred oxidants are oxygen and air.

The aldehydes can be used as such or as a solution in a solvent which is inert under the reaction conditions. Examples of suitable solvents are ketones such as acetone, esters, e.g. ethyl acetate, hydrocarbons, e.g. toluene, and nitrohydrocarbons such as nitrobenzene. The concentration of the aldehyde is limited by its solubility in the solvent.

The process of the invention can be carried out batchwise or continuously. Recirculation of unreacted reaction participants is possible in both cases.

The pure carboxylic acid is isolated from the crude acid mixture obtained after the oxidation by means of distillation under customary conditions. The distillation residue comprising the alkali metal carboxylates or alkaline earth metal carboxylates and catalytic metals is separated off and can be added again to the starting aldehyde, if appropriate after addition of fresh alkali metal carboxylates or alkaline earth metal carboxylates or alkali metal compounds or alkaline earth metal compounds which are converted into the carboxylates under the reaction conditions and also of catalytically active metals.

In a useful embodiment of the process of the invention, the aldehyde together with the alkali metal carboxylates or alkaline earth metal carboxylates and the catalytic metal are placed in a suitable reactor, e.g. a tube reactor which is provided with an inflow plate and may also contain packing, and the oxygen or the oxygen-containing gas mixture is passed from below through the aldehyde.

In a further embodiment, a trickle tower containing packing is used as reactor. The aldehyde containing alkali metal carboxylates or alkaline earth metal carboxylates and catalytic metal is allowed to trickle down over the packing and oxygen or an oxygen-containing gas mixture is simultaneously introduced into the tower in cocurrent or countercurrent.

The following examples describe the preparation of n-pentanoic acid and isononanoic acid by the process claimed.

The reaction of the starting aldehydes is carried out in accordance with the invention in the presence of alkali metal carboxylates or alkaline earth metal carboxylates and of metals of groups 5 to 11 of the Periodic Table or compounds of these metals as catalysts. The results of comparative examples in which the aldehydes were oxidized without any additives, only with addition of alkali metal carboxylates or alkaline earth metal carboxylates and only with addition of catalytic metals are compared with the examples.

The respective experimental results are reported by way of the following parameters:
aldehyde conversion;
selectivity, calculated from the proportion of carboxylic acid in the reaction product, based on aldehyde reacted;
yield of carboxylic acid.

Of course, the novel process is not restricted to the embodiment described below.

EXAMPLES

Oxidation of n-Pentanal

Comparative Example 1 (without Addition of Alkali Metal and Metal)

The liquid-phase oxidation of n-pentanal to n-pentanoic acid was carried out without addition of catalyst in a bubble column reactor made of glass which had an internal diameter of 38 mm and a length of 150 cm. Depending on the reaction behavior, the reactor was cooled or heated via its wall by means of a water circuit connected to a heat exchanger and the internal temperature was kept constant in this way. The oxygen was fed in from below through a glass filter plate which was joined to the bubble column and had a maximum pore width of 16–40 μm.

A mixture of 765.0 g of n-pentanal and 35.0 g of n-pentanoic acid was used in the oxidation. According to analysis by gas chromatography (GC analysis), the aldehyde had the following composition:
0.01% of fore-run components
0.23% of 2-/3-methylbutanal
99.62% of n-pentanal
0.11% of n-pentanol
0.03% of n-pentanoic acid After oxidation for 6 hours at a constant 50° C. and a total oxygen input of 120% of theory, based on aldehyde used, the following results were determined:
GC analysis 0.20% of fore-run components
3.28% of n-pentanal
0.20% of 2-/3-methylbutyric acid
95.42% of n-pentanoic acid
0.90% of other components The conversion of n-pentanal is 96.0% of theory, and the associated selectivity to the formation of n-pentanoic acid is 99.0% of theory.

A yield of 95.0% can be calculated from this. The carboxylic acid originally present in the starting material for the oxidation was taken into account in the calculation of the result.

Comparative Example 2 (without Addition of Metal)

This experiment was carried out under the conditions of comparative example 1 but with not only n-pentanoic acid (29.5 g) but also a catalyst solution comprising 2.50 g of potassium n-pentanoate, 5.47 g of n-pentanoic acid and 1.32 g of water being added to the aldehyde starting material (765.0 g). The molar ratio of n-pentanal to potassium was 1000:2.

After oxidation for 6 hours at a constant 50° C. and a total oxygen input of 120% of theory, based on aldehyde used, the following results were determined:
GC analysis: 0.12% of fore-run components
3.97% of n-pentanal
0.16% of 2-/3-methylbutyric acid
95.28% of n-pentanoic acid
0.47% of other components The conversion of n-pentanal is 95.1% of theory, and the associated selectivity to the formation of n-pentanoic acid is 99.6% of theory.

A yield of 94.7% can be calculated from this. The carboxylic acid originally present in the starting material for the oxidation was taken into account in the calculation of the result.

Comparative Example 3 (without Addition of Metal)

Comparative example 2 was repeated but with not only n-pentanoic acid (21.4 g) but also a catalyst solution comprising 6.22 g of potassium n-pentanoate, 13.59 g of n-pentanoic acid and 3.29 g of water being added to the aldehyde starting material (765.0 g). The molar ratio of n-pentanal to potassium was 1000:5.

After oxidation for 6 hours at a constant 50° C. and a total oxygen input of 120% of theory, based on aldehyde used, the following results were determined:

GC analysis: 0.11% of fore-run components
  4.76% of n-pentanal
  0.20% of 2-/3-methylbutyric acid
  94.49% of n-pentanoic acid
  0.44% of other components The conversion of n-pentanal is 94.2% of theory, and the associated selectivity to the formation of n-pentanoic acid is 99.6% of theory.

A yield of 93.8% can be calculated from this. The carboxylic acid originally present in the starting material for the oxidation was taken into account in the calculation of the result.

Comparative Example 4 (without Addition of Alkali Metal)

This experiment was carried out under the conditions of comparative example 1 but with not only n-pentanoic acid (25.0 g) but also 10.0 g of n-pentanoic acid containing 0.49 mg of Fe as catalyst solution being added to the aldehyde starting material (765.0 g). Based on the aldehyde, the iron addition was 0.63 ppm.

After oxidation for 6 hours at a constant 50° C. and a total oxygen input of 120% of theory, based on aldehyde use, the following results were determined:
GC analysis: 0.47% of fore-run components
  0.82% of n-pentanal
  0.20% of 2-/3-methylbutyric acid
  97.22% of n-pentanoic acid
  1.29% of other components The conversion of n-pentanal is 99.0% of theory, and the associated selectivity to the formation of n-pentanoic acid is 98.3% of theory.

A yield of 97.3% can be calculated from this. The carboxylic acid originally present in the starting material for the oxidation was taken into account in the calculation of the result.

Comparative Example 5 (without Addition of Alkali Metal)

Comparative example 4 was repeated but with not only n-pentanoic acid (15.0 g) but also 20.0 g of n-pentanoic acid containing 0.97 mg of Fe as catalyst solution being added to the aldehyde starting material (765.0 g). Based on the aldehyde, the iron addition was 1.27 ppm.

After oxidation for 6 hours at a constant 50° C. and a total oxygen input of 120% of theory, based on aldehyde use, the following results were determined:
GC analysis: 0.49% of fore-run components
  0.63% of n-pentanal
  0.21% of 2-/3-methylbutyric acid
  96.89% of n-pentanoic acid
  1.78% of other components The conversion of n-pentanal is 99.2% of theory, and the associated selectivity to the formation of n-pentanoic acid is 97.8% of theory.

A yield of 97.0% can be calculated from this. The carboxylic acid originally present in the starting material for the oxidation was taken into account in the calculation of the result.

Example 1

This experiment was carried out under the conditions of comparative example 1 but with not only n-pentanoic acid (19.5 g) but also two catalyst solutions being added to the aldehyde starting material (765.0 g). Catalyst solution A comprised 2.50 g of potassium n-petanoate, 5.47 g of n-pentanoic acid and 1.32 g of water, while 10.0 g of n-pentanoic acid containing 0.49 mg of Fe were used as catalyst solution B.

The molar ratio of n-pentanal to potassium was thus 1000:2; based on the aldehyde, the iron addition was 0.63 ppm.

After oxidation for 6 hours at a constant 50° C. and a total oxygen input of 120% of theory, based on aldehyde use, the following results were determined:
GC analysis: 0.16% of fore-run components
  0.74% of n-pentanal
  0.21% of 2-/3-methylbutyric acid
  98.22% of n-pentanoic acid
  0.67% of other components The conversion of n-pentanal is 99.1% of theory, and the associated selectivity to the formation of n-pentanoic acid is 99.3% of theory.

A yield of 98.4% can be calculated from this. The carboxylic acid originally present in the starting material for the oxidation was taken into account in the calculation of the result.

Examples 2–4

Examples 2 to 4 were carried out under the conditions of example 1 but with different amounts of catalyst solution A and B being added to the aldehyde starting material (765.0 g). Further details may be found in Table 1.

TABLE 1

Oxidation of n-pentanal in the presence of alkali metal and metal

| Experiment | 2 | 3 | 4 |
|---|---|---|---|
| Amount of n-pentanal used (g) | 765.0 | 765.0 | 765.0 |
| Amount of catalyst solution A used (g) | 9.3 | 23.1 | 23.1 |
| Amount of catalyst solution B used (g) | 20.0 | 10.0 | 20.0 |
| Composition of catalyst solution A | | | |
| potassium n-pentanoate (g) | 2.50 | 6.22 | 6.22 |
| n-pentanoic acid (g) | 5.47 | 13.59 | 13.59 |
| water (g) | 1.32 | 3.29 | 3.29 |
| Composition of catalyst solution B | | | |
| n-pentanoic acid (g) | 20.0 | 10.0 | 20.0 |
| iron (mg) | 0.97 | 0.49 | 0.97 |
| Molar ratio of n-pentanal to potassium | 1000:2 | 1000:5 | 1000:5 |
| Iron addition based on n-pentanal (ppm) | 1.27 | 0.63 | 1.27 |
| GC analysis of the crude acid | | | |
| fore-run components (%) | 0.17 | 0.16 | 0.16 |
| n-pentanal (%) | 0.61 | 0.88 | 0.60 |
| 2-/3-methylbutyric acid (%) | 0.21 | 0.21 | 0.22 |
| n-pentanoic acid (%) | 98.23 | 98.15 | 98.38 |
| other components (%) | 0.78 | 0.60 | 0.64 |
| Conversion of n-pentanal (% of theory) | 99.2 | 98.9 | 99.3 |
| Selectivity to n-pentanoic acid (% of theory) | 99.2 | 99.4 | 99.3 |
| Yield of n-pentanoic acid (% of theory) | 98.4 | 98.3 | 98.6 |

Oxidation of Isononanal

Comparative Example 6 (without Addition of Alkali Metal and Metal)

The liquid-phase oxidation of isononanal to isononanoic acid was carried out without addition of catalyst in a bubble column reactor made of glass which had an internal diameter of 38 mm and a length of 150 cm.

Depending on the reaction behavior, the reactor was cooled or heated via its wall by means of a water circuit connected to a heat exchanger and the internal temperature was kept constant in this way. The oxygen was fed in from below through a glass filter plate which was joined to the bubble column and had a maximum pore width of 16–40 µm.

A mixture of 700.0 g of isononanal and 100.0 g of isononanoic acid was used in the oxidation. According to analysis by gas chromatography (GC analysis), the aldehyde had the following composition:

0.16% of fore-run components
94.41% of 3,5,5-trimethylhexanal
5.24% of isomeric $C_9$-aldehydes
0.04% of 3,5,5-trimethylhexanoic acid
0.15% of other components After oxidation for 6 hours at a constant 60° C. and a throughput of 20 liters of oxygen/hour, the following results were determined:
GC analysis 0.58% of fore-run components
1.74% of 3,5,5-trimethylhexanal
0.07% of isomeric $C_9$-aldehydes
90.81% of 3,5,5-trimethylhexanoic acid
5.35% of isomeric $C_9$-acids
1.45% of other components The conversion (based on the main component 3,5,5-trimethylhexanal) is 97.7% of theory, and the associated selectivity to the formation of 3,5,5-trimethylhexanoic acid is 97.7% of theory.

A yield of 95.5% can be calculated from this. The carboxylic acid originally present in the starting material for the oxidation was taken into account in the calculation of the result.

Comparative Example 7 (without Addition of Metal)

This experiment was carried out under the conditions of comparative example 6 but with not only isononanoic acid (88.3 g) but also a catalyst solution comprising 4.82 g of potassium isononanoate, 11.66 g of isononanoic acid and 1.82 g of water being added to the aldehyde starting material (700.0 g). The molar ratio of n-pentanal to potassium was 1000:5.

After oxidation for 6 hours at a constant 60° C. and a throughput of 20 liters of oxygen/hour, the following results were determined:
GC analysis 0.28% of fore-run components
0.97% of 3,5,5-trimethylhexanal
0.10% of isomeric $C_9$-aldehydes
92.54% of 3,5,5-trimethylhexanoic acid
5.69% of isomeric $C_9$-acids
0.42% of other components The conversion (based on the main component 3,5,5-trimethylhexanal) is 98.7% of theory, and the associated selectivity to the formation of 3,5,5-trimethylhexanoic acid is 98.9% of theory.

A yield of 97.6% can be calculated from this. The carboxylic acid originally present in the starting material for the oxidation was taken into account in the calculation of the result.

Comparative Example 8 (without Addition of Alkali Metal)

This experiment was carried out under the conditions of comparative example 6 but with not only isononanoic acid (11.7 g) but 88.3 g of isononanoic acid containing 0.51 mg of Fe as catalyst solution being added to the aldehyde starting material (700.0 g). Based on the aldehyde, the iron addition was 0.73 ppm.

After oxidation for 6 hours at a constant 60° C. and a throughput of 20 liters of oxygen/hour, the following results were determined:
GC analysis 0.95% of fore-run components
0.56% of 3,5,5-trimethylhexanal
0.13% of isomeric $C_9$-aldehydes
91.46% of 3,5,5-trimethylhexanoic acid
5.37% of isomeric $C_9$-acids
1.53% of other components The conversion (based on the main component 3,5,5-trimethylhexanal) is 99.3% of theory, and the associated selectivity to the formation of 3,5,5-trimethylhexanoic acid is 97.1% of theory.

A yield of 96.4% can be calculated from this. The carboxylic acid originally present in the starting material for the oxidation was taken into account in the calculation of the result.

Example 5

This experiment was carried out under the conditions of comparative example 6 but with two catalyst solutions being additionally added to the aldehyde starting material (700.0 g). Catalyst solution A comprised 4.82 g of potassium isononanoate, 11.66 g of isononanoic acid and 1.82 g of water, while 88.3 g of isononanoic acid containing 0.51 mg of Fe were used as catalyst solution B.

The molar ratio of isononanal to potassium was 1000:5; based on the aldehyde, the iron addition was 0.73 ppm.

After oxidation for 6 hours at a constant 60° C. and a throughput of 20 liters of oxygen/hour, the following results were determined:
GC analysis 0.38% of fore-run components
0.22% of 3,5,5-trimethylhexanal
0.08% of isomeric $C_9$-aldehydes
93.21% of 3,5,5-trimethylhexanoic acid
5.66% of isomeric $C_9$-acids
0.45% of other components The conversion (based on the main component 3,5,5-trimethylhexanal) is 99.7% of theory, and the associated selectivity to the formation of 3,5,5-trimethylhexanoic acid is 98.8% of theory.

A yield of 98.5% can be calculated from this. The carboxylic acid originally present in the starting material for the oxidation was taken into account in the calculation of the result.

The results of the comparative examples and the results of the examples according to the invention are summarized in tables 2 and 3 below.

TABLE 2

Oxidation of n-pentanal

| Experiment | Potassium addition [mmol of potassium] per mole of aldehyde | Iron addition [ppm of iron] | n-Pentanal conversion % | Selectivity to n-pentanoic acid % | Yield of n-pentanoic acid % |
| --- | --- | --- | --- | --- | --- |
| Comparison 1 | none | none | 96.0 | 99.0 | 95.0 |
| Comparison 2 | 2 | none | 95.1 | 99.6 | 94.7 |
| Comparison 3 | 5 | none | 94.2 | 99.6 | 93.8 |
| Comparison 4 | none | 0.63 | 99.0 | 98.3 | 97.3 |
| Comparison 5 | none | 1.27 | 99.2 | 97.8 | 97.0 |
| Example 1 | 2 | 0.63 | 99.1 | 99.3 | 98.4 |
| Example 2 | 2 | 1.27 | 99.2 | 99.2 | 98.4 |
| Example 3 | 5 | 0.63 | 98.9 | 99.4 | 98.3 |
| Example 4 | 5 | 1.27 | 99.3 | 99.3 | 98.6 |

TABLE 3

Oxidation of isononanal

| Experiment | Potassium addition [mmol of potassium] per mole of aldehyde | Iron addition [ppm of iron] | Isononanal conversion % | Selectivity to isononanoic acid % | Yield of isononanoic acid % |
| --- | --- | --- | --- | --- | --- |
| Comparison 6 | none | none | 97.7 | 97.7 | 95.5 |
| Comparison 7 | 5 | none | 98.7 | 98.9 | 97.6 |
| Comparison 8 | none | 0.73 | 99.3 | 97.1 | 96.4 |
| Example 5 | 5 | 0.73 | 99.7 | 98.8 | 98.5 |

As comparison of the examples demonstrates, the conversion behavior in the oxidation of aliphatic straight-chain or β-alkyl-branched aldehydes to the corresponding carboxylic acids can be improved with a simultaneous increase in the selectivity if the oxidation is carried out in the presence of alkali metal carboxylates or alkaline earth metal carboxylates and catalytically active metals.

What we claim is:

1. A process for preparing aliphatic straight-chain and β-alkyl-branched carboxylic acids of 5 to 13 carbon atoms comprising oxidizing the corresponding aldehydes with oxygen or oxygen-containing gas mixtures at 20 to 100° C., in the presence of alkali metal carboxylates or alkaline earth metal carboxylates or a mixture thereof in an amount, calculated as alkali or alkaline earth metal, of from 1 mmol to 10 mmol each per mole of aldehyde used and in the presence of 0.1 to 5.0 ppm of a metal of groups 5 to 11 of the Periodic Table of the Elements or the corresponding amount of a compound of such a metal or a mixture of such metals and/or metal compounds, based on the aldehyde used.

2. The process of claim 1, wherein the oxidation of the aldehydes is carried out in the presence of alkali metal carboxylates or alkaline earth metal carboxylates or a mixture thereof in an amount, calculated as alkali or alkaline earth metal, of 1 mmol to 8 mmol each, per mole of aldehyde used and in the presence of from 0.2 to 3 ppm, of a metal of groups 5 to 11 of the Periodic Table of the Elements or the corresponding amount of a compound of such a metal or a mixture of such metals and/or metal compounds, based on the aldehyde used.

3. The process of claim 2 with 1 to 5 mmol of carboxylate and 0.5 to 2 ppm of metal.

4. The process of claim 1, wherein lithium, sodium or potassium carboxylates are used as alkali metal carboxylates and magnesium, calcium and bartium carboxylates are used as alkaline earth metal carboxylates.

5. The process of claim 3, wherein the alkali metal carboxylates or alkaline earth metal carboxylates are salts of the carboxylic acids which are formed as a result of the oxidation of the aldehydes used.

6. The process of claim 1, wherein the metal of groups 5 to 11 of the Periodic Table of the Elements is selected from the group consisting of vanadium, chromium, molybdenum, iron, cobalt, nickel, ruthenium, rhodium, palladium and copper.

7. The process of claim 6, wherein the metal is iron or rhodium.

8. The process of claim 1, wherein the metal compounds are derived from metals selected from the group consisting of vanadium, chromium, molybdenum, iron, cobalt, nickel ruthenium, rhodium, palladium and copper.

9. The process of claim 8, wherein the metal is iron or rhodium.

10. The process of claim 1, wherein the metal compounds are selected from the group consisting of, carboxylates, acetylacetonates and carbonyl compounds.

11. The process of claim 10, wherein the metal carboxylates are salts of the carboxylic acids which are formed as a result of the oxidation of the aldehydes used.

12. The process of claim 1, wherein the oxidation is carried out at temperatures in the range of 20 to 80° C.

13. The process of claim 12, wherein the temperature is 40 to 80° C.

14. The process of claim 1, wherein the oxidation is carried out at pressures from atmospheric pressure to 1.0 MPa.

15. The process of claim 14, wherein the pressure is up to 0.8 MPa.

16. The process of claim 1, wherein the oxygen-containing gas mixtures have a proportion of up to 90% by volume of inert constituents.

17. The process of claim 16 with a proportion of 30 to 80% by volume of inert constituents.

* * * * *